(12) United States Patent
Tanaka et al.

(10) Patent No.: US 8,760,974 B2
(45) Date of Patent: Jun. 24, 2014

(54) ULTRASONIC PROBE AND ULTRASONIC IMAGING APPARATUS

(75) Inventors: Hiroki Tanaka, Musashino (JP); Takashi Azuma, Sagamihara (JP)

(73) Assignee: Hitachi Medical Corporation, Tokyo (JP)

( * ) Notice: Subject to any disclaimer, the term of this patent is extended or adjusted under 35 U.S.C. 154(b) by 266 days.

(21) Appl. No.: 13/265,455

(22) PCT Filed: Apr. 19, 2010

(86) PCT No.: PCT/JP2010/056938
§ 371 (c)(1),
(2), (4) Date: Oct. 20, 2011

(87) PCT Pub. No.: WO2010/122982
PCT Pub. Date: Oct. 28, 2010

(65) Prior Publication Data
US 2012/0038242 A1    Feb. 16, 2012

(30) Foreign Application Priority Data
Apr. 21, 2009   (JP) .................................. 2009-103271

(51) Int. Cl.
*G10K 9/12*   (2006.01)

(52) U.S. Cl.
CPC ..................... *G10K 9/121* (2013.01)
USPC .......................................... 367/174; 367/181

(58) Field of Classification Search
USPC ................................................ 367/174, 181
See application file for complete search history.

(56) References Cited

U.S. PATENT DOCUMENTS

| | | | |
|---|---|---|---|
| 6,262,946 B1 | 7/2001 | Khuri-Yakub et al. | |
| 6,359,367 B1 | 3/2002 | Sumanaweera et al. | |
| 6,714,484 B2 | 3/2004 | Ladabaum et al. | |
| 2003/0103412 A1* | 6/2003 | Ladabaum et al. | 367/162 |
| 2004/0000847 A1* | 1/2004 | Ladabaum et al. | 310/367 |
| 2007/0164631 A1* | 7/2007 | Adachi et al. | 310/311 |
| 2008/0015441 A1* | 1/2008 | Kanda et al. | 600/459 |
| 2008/0037808 A1* | 2/2008 | Sawada et al. | 381/190 |
| 2008/0048211 A1* | 2/2008 | Khuri-Yakub et al. | 257/204 |
| 2009/0076393 A1 | 3/2009 | Adachi et al. | |

FOREIGN PATENT DOCUMENTS

| | | |
|---|---|---|
| CN | 101014289 | 8/2007 |
| JP | 2006-319712 | 11/2006 |
| JP | 2007-229327 | 9/2007 |
| JP | 2008-193357 | 8/2008 |

OTHER PUBLICATIONS

International Search Report and Written Opinion for PCT International Application No. PCT/JP2010/056938, mailed Jul. 13, 2010.

* cited by examiner

*Primary Examiner* — Luke Ratcliffe
*Assistant Examiner* — Hovhannes Baghdasaryan
(74) *Attorney, Agent, or Firm* — Brundidge & Stanger, P.C.

(57) ABSTRACT

Artifacts due to lateral wave that occurs in a substrate of a Capacitive Micro-machined Ultrasonic Transducer is reduced. The substrate thickness of the ultrasonic transducer is set in an optimum range to efficiently radiate the energy of lateral wave in the sensitive band 91 of the ultrasonic transducer to the outside so that the lateral wave is attenuated thereby reducing the artifacts in ultrasonic imaging.

15 Claims, 12 Drawing Sheets

ULTRASONIC PROBE AND ULTRASONIC IMAGING APPARATUS

TECHNICAL FIELD

The present invention relates to an ultrasonic probe and an ultrasonic imaging device, and particularly to an ultrasonic probe and an ultrasonic imaging device using a Capacitive Micro-machined Ultrasonic Transducer.

BACKGROUND ART

The ultrasonic transducer is a device for performing the radiation and reception of sound waves beyond the audible range (about 20 Hz to 20 kHz) and is widely used in medical applications, non-destructive inspection, and the like. Currently, the most extensively used as the ultrasonic transducer are piezoelectric devices typified by PZT (Lead Zirconate Titanate). However, in recent years, ultrasonic devices called Capacitive Micro-machined Ultrasonic Transducers (hereafter, referred as CMUTs), which are based on an operation principle different from that of piezoelectric type devices, have been developed and are being put into practical uses. The CMUT are fabricated by applying semiconductor technology. In general, they are formed by embedding an electrode material into a substrate made up of a member that is used in semiconductor process, such as silicon (the substrate itself may provide the electrode), and securing a minute (for example, 50 µm) and thin (for example, several µm) diaphragm with supporting posts surrounding the diaphragm. A cavity is provided between the diaphragm and the substrate such that the diaphragm can vibrate. An electrode material is also embedded in the diaphragm. Thus, disposing separate electrodes in the substrate and the diaphragm allows the structure to function as a capacitor. Further, applying voltage to both the electrodes (generally, a bias voltage is applied in advance) makes it operate as an ultrasonic transducer. Applying alternating-current voltage (AC voltage) to both the electrodes varies the electrostatic force between the electrodes, thereby causing the diaphragm to vibrate. If, at this moment, any medium is present in contact with the diaphragm, the vibration of the diaphragm propagates in the medium as a sound wave. That is, it is possible to radiate sound. Conversely, if a sound wave is transmitted to the diaphragm, the diaphragm vibrates in response thereto, thereby changing the distance between both the electrodes so that an electric signal flows between both the electrodes. Thus, it is possible to receive the sound wave by taking out the electric signal.

The diaphragm of CMUT is dynamically connected to the underlying substrate via the supporting posts. Therefore, when the diaphragm vibrates, the vibration propagates not only to the medium but also to the substrate. Alternatively, the electrostatic force generated between the electrodes of diaphragm side and substrate side acts equally on both the diaphragm and the substrate. Thus, electric vibration propagates to the substrate through electrostatic force. In this way, in a CMUT, vibration will propagate not only to the diaphragm, but also to the substrate by way of dynamic or electrical action. This vibration propagating through the substrate is reflected from the substrate toward the diaphragm side, and is detected again as an electric signal. These signals will become undesired response in performing normal ultrasonic transmission/reception. These undesired responses will become artifacts in an ultrasonic imaging device for medical use and a non-destructive inspection apparatus, and increase the risk of erroneously evaluating diagnoses and inspection results. Therefore, in using the CMUT, suppression of signal components of the vibration through the substrate will become extremely important. Patent Literature 1 describes that the effect of artifact signals is avoided by reducing the substrate thickness to not more than a certain thickness so that frequency components of the signal which can provide artifact components are brought out from the sensitive band of the transducer. Moreover, Patent Literature 2 describes a technique to avoid the directivity of ultrasonic wave from deteriorating due to a lateral wave excited in the substrate by optimizing the substrate thickness and providing a slot and porous in the substrate.

CITATION LIST

Patent Literature

Patent Literature 1: U.S. Pat. No. 6,714,484
Patent Literature 2: U.S. Pat. No. 6,262,946
Patent Literature 3: U.S. Pat. No. 6,359,367

SUMMARY OF INVENTION

Technical Problem

There are various modes of vibration in the vibration that is generated in the substrate. They are broadly divided into longitudinal waves and lateral/shear waves. The longitudinal wave is propagated through a medium that transmits sound while the medium is repeatedly compressed and expanded in the traveling direction of the wave. A longitudinal wave becomes an undesired response when a vibration generated near the diaphragm is reflected at a boundary between different acoustic impedances such as the back side of the substrate, and thereafter gets back to the diaphragm side to be detected as an electric signal; or when a reflection signal is radiated from the diaphragm to disturb the properties of radiated sound wave or to be directly propagated to an adjacent diaphragm thereby causing a similar phenomenon. Among those described above, in the case of the reflection wave, multiple reflection is repeated in the substrate. This is because the attenuation coefficient of a sound wave is very small in silicon which is typically used for the member of the substrate, and the sound wave will not sufficiently attenuate within the member while the sound propagates. The frequency of such multiple reflection is determined from the longitudinal-wave sound velocity and the thickness of the substrate. When the longitudinal-wave sound velocity is a fixed value, as the substrate thickness is reduced, the round trip time of sound becomes shorter, that is, the time period of multiple reflection becomes shorter and the multiple reflection frequency (the reciprocal of the time period of multiple reflection) becomes higher. Patent Literature 1 describes a technique to avoid the effect of undesired response by reducing the substrate thickness to not more than a certain thickness to increase the multiple reflection frequency caused by longitudinal wave so that this effect is shifted toward a higher frequency side of the band (about 1 MHz to 10 MHz) used in medical ultrasonic wave.

On one hand, there exists a lateral wave (bending wave) in the substrate. The lateral wave propagates while the bending of a plate gradually transmits to the surrounding. Therefore, the traveling direction of sound and the deformation direction of the substrate are orthogonal to each other. When such a lateral wave propagates in the substrate without being attenuated, the vibration thereof causes the diaphragm around the sound source to vibrate thereby generating artifacts. Therefore, in using a CMUT, it is necessary to avoid the effects of not only longitudinal waves but also lateral waves. However, Patent Literature 1 does not present any configuration for avoiding the effects of such lateral waves. It is an object of the present invention to eliminate signal components of lateral wave from the sensitive band in the ultrasonic probe by efficiently radiating the energy of a frequency region specific to the lateral wave outside the substrate, thereby reducing the artifact signal components. Although Patent Literature 2 addresses lateral waves and surface waves, in which a lateral wave and a longitudinal wave are combined to vibrate, as in the present invention, it intends to reduce the effect on the directivity of ultrasonic wave and to suppress the propagation of lateral wave in the substrate by controlling the angle at which a lateral wave is radiated. Therefore, its effects are different from those of the present invention and, as a matter of course, the solution to the problem and the optimum configuration is different as well.

Solution to Problem

Attenuation of lateral wave is realized by efficiently radiating the energy of lateral waves in the sensitive band of CMUT to outside of the transducer by setting the substrate thickness of CMUT within an optimum range.

Since a material (for example, silicon) which is used as the substrate of CMUT has a low attenuation coefficient of sound in the material, there is no other way to attenuate vibration energy but to radiate energy to the outside. The efficiency of radiating a lateral wave generated in a substrate to the outside is determined from the relation between the longitudinal-wave sound velocity of a medium adjacent to the substrate and the lateral-wave sound velocity of the substrate, and has a frequency dependence. The frequencies of highest radiation energy efficiency are around an inherent frequency called as a coincidence frequency and in its higher frequency side. Therefore, to efficiently attenuate the lateral wave in the sensitive band of CMUT, it is effective to cause a frequency band of high radiation energy efficiency around the coincidence frequency to overlap the sensitive band of CMUT. The present invention presents a method for determining a coincidence frequency from physical parameters of a CMUT and the medium in contact therewith, and setting an optimum substrate thickness such that the coincidence frequency overlaps the sensitive band of CMUT.

An ultrasonic probe of the present invention includes a Capacitive Micro-machined Ultrasonic Transducer which includes a substrate having a first electrode and a diaphragm having a second electrode, wherein the diaphragm is secured at its peripheral edge to the substrate by a supporting wall which rises from the substrate, and a cavity is formed between the substrate and the diaphragm, wherein the ultrasonic probe is configured to set the substrate thickness such that a lateral-wave sound velocity that propagates in the substrate is not less than the longitudinal-wave sound velocity of a medium in contact with the substrate or the diaphragm at least in a fractional frequency band within a sensitive band of the ultrasonic probe.

Further, an ultrasonic probe of the present invention includes a Capacitive Micro-machined Ultrasonic Transducer which includes a substrate having a first electrode and a diaphragm having a second electrode, wherein the diaphragm is secured at its peripheral edge to the substrate by a supporting wall which rises from the substrate, and a cavity is formed between the substrate and the diaphragm, and at least one or more acoustic medium in contact with the Capacitive Micro-machined Ultrasonic Transducer; and the thickness h of the substrate is set such that a coincidence frequency of the ultrasonic probe satisfies the following conditions:

[Expression 1]

$$c_{sub} = \frac{\omega}{k_{sub}} \quad (1)$$

$$\omega = 2\pi f$$

$$k_{sub} = \frac{\sqrt{\omega}}{\alpha}$$

$$\alpha^2 = \sqrt{\frac{Eh^2}{12\rho_{sub}(1-\upsilon^2)}}$$

Where, $c_{sub}$ is a lateral wave velocity [m/s] of plate, $\omega$ is an angular velocity [rad/s], f is a frequency [Hz], $k_{sub}$ is a wave number of the lateral wave of the substrate, E is a Young's modulus [Pa] of the substrate, h is a thickness [m] of the substrate, $\rho_{sub}$ is a density [kg/m$^3$] of the substrate, and $\upsilon$ is a Poisson's ratio of the substrate. Moreover, a radiation energy efficiency with respect to an acoustic medium in contact with the transducer is proportional to the following equation $\eta(f)$:

[Expression 2]

$$\eta(f) = \frac{c_{sub}}{\sqrt{c_{sub}^2 - c^2}} \quad (2)$$

Where, c is the longitudinal-wave sound velocity of either of the acoustic media in contact with the transducer. At this time, $$c_{sub} > c \quad (3)$$

and letting the transmission/reception sensitivity of the transducer be G(f), it has a substrate thickness h that maximizes the following term:

[Expression 3]

$$F = \int \{\eta(f) \times G(f)\} df \quad (4)$$

Moreover, letting $f_{co}$ represented by Equation (5) be the coincidence frequency, the ultrasonic probe of the present invention satisfies the condition of Equation (6).

$$f_{co} = f|(c_{sub} = c) \quad (5)$$

$$f_{lc} \leq f_{co} \leq f_{hc} \quad (6)$$

Where, $f_{lc}$ and $f_{hc}$ are a lower cut-off frequency and a higher cut-off frequency of the transmission/reception sensitivity G(f) of the transducer, respectively.

Advantageous Effects of Invention

The present invention can suppress undesired response components and prevent artifacts by causing the lateral wave that propagates in the substrate of CMUT to be actively and efficiently radiated to outside the substrate.

DESCRIPTION OF EMBODIMENTS

Hereafter, embodiments for practicing the present invention will be described.

First Embodiment

Figure 1:
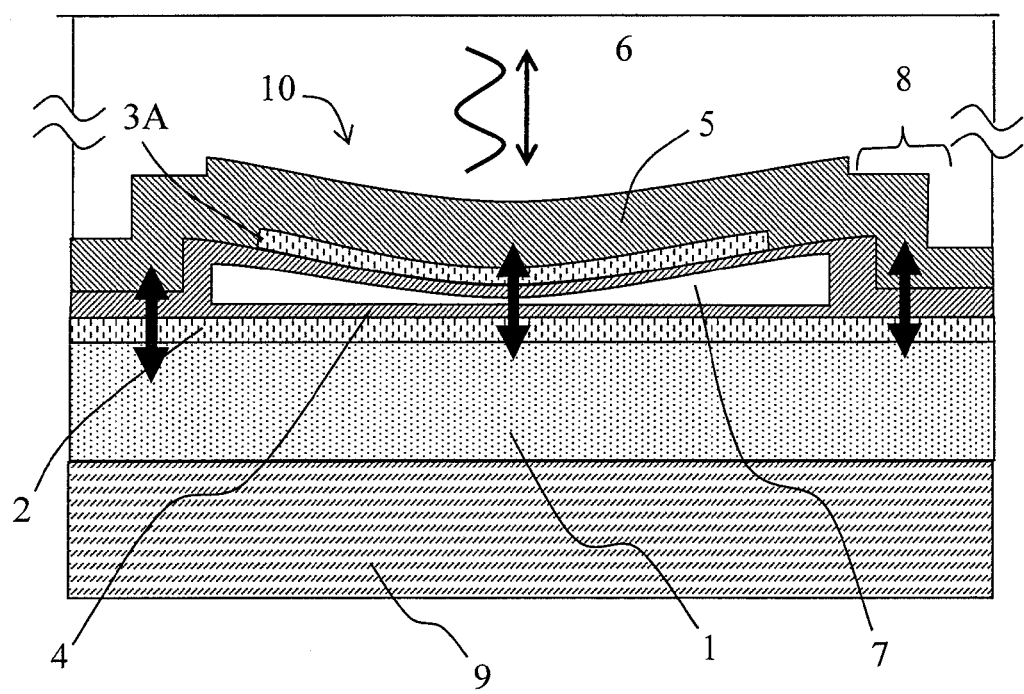
FIG. 1 is a schematic cross sectional view of a Capacitive Micro-machined Ultrasonic Transducer.
Figure 2:
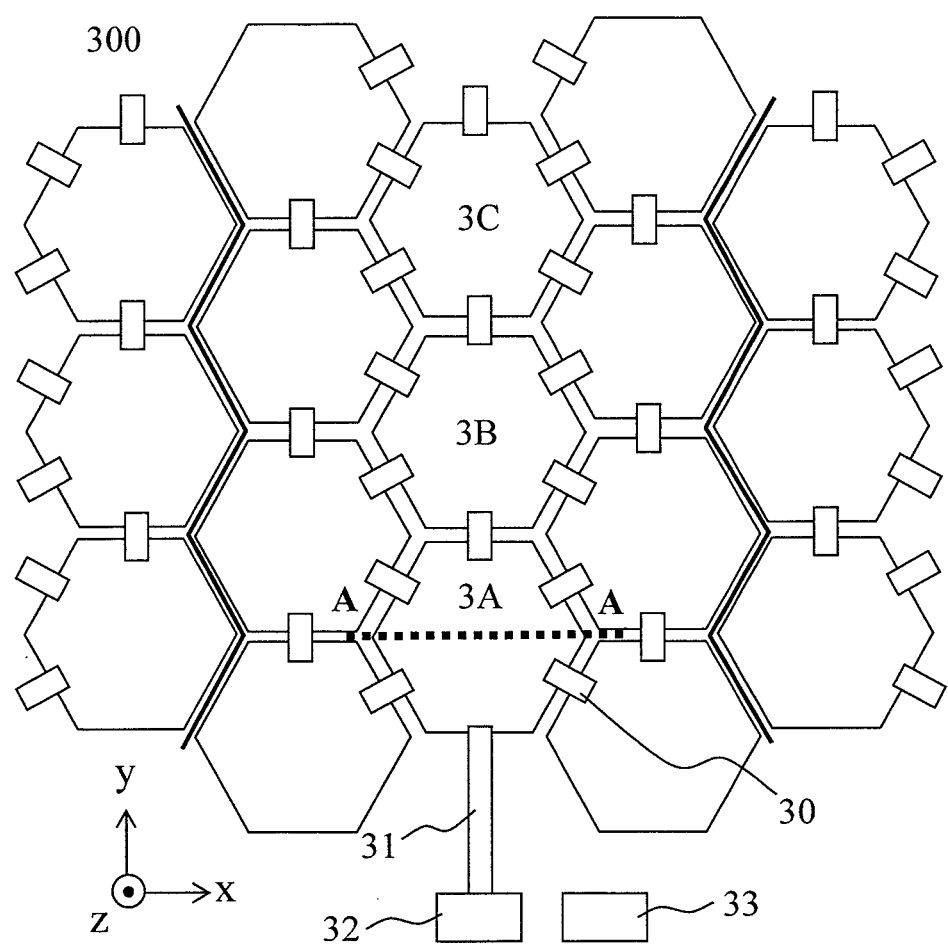
FIG. 2 is a schematic plan view of a Capacitive Micromachined Ultrasonic Transducer array.

FIG. 1 is a vertical cross sectional view of a first embodiment of CMUT (10), and FIG. 2 is a plan view thereof. The A-A section in FIG. 2 corresponds to FIG. 1. FIG. 2 indicates the top of the plane 3A of FIG. 1. It is noted that for the sake of convenience of description, the direction in which the CMUT (10) transmits ultrasonic wave, that is, upward in FIG. 1 and a vertically upward direction with respect to the plane of the page of FIG. 2 are supposed to be a z direction. Moreover, the right hand directions of FIGS. 1 and 2 are supposed to be an x direction, and vertically downward direction with respect to the plane of the page of FIG. 1 and the upward direction of FIG. 2 are supposed to be a y direction.

As shown in FIGS. 1 and 2, the CMUT (10) is configured such that a thin-film like lower electrode 2 made up of a conductor such as aluminum and tungsten is formed on a planar substrate 1 made up of an insulator or semiconductor such as a silicon single crystal, and a diaphragm 5 is formed on the lower electrode 2. The silicon substrate may be used as the lower electrode at the same time. The diaphragm 5 is secured at its peripheral edge to the substrate with a supporting wall 8 that rises from the substrate, and a cavity 7, of which periphery is sealed tightly by the supporting wall 8, is formed between the diaphragm 5 and the substrate 1. An upper electrode 3A coated with an insulator 4 is disposed in the diaphragm 5. The upper electrode 3A is displaced toward the substrate by an electrostatic force when a voltage is applied between the lower electrode 2 and the upper electrode 3A. In order to prevent the conduction when the upper electrode 3A is displaced excessively and comes into contact with the lower electrode 2, a top portion of the lower electrode 2 or the upper electrode 3A is preferably coated with the insulator 4. In an actual use of the CMUT, the surface of the diaphragm 5 is brought into contact with any acoustic medium 6 that propagates ultrasonic wave such as air and water typically. Moreover, a backside material (backing material) 9 for the purpose of sound attenuation may be bonded to the underside of the substrate 1.

FIG. 2 shows a CMUT array 300 in which supposing the CMUT (10) as being one element, a numerous similar elements are placed in an array. In this way, the CMUT can be used not only in a single element, but also in an array of multiple elements. Moreover, the upper electrodes (3A, 3B, and 3C in FIG. 2) of multiple elements can be electrically interconnected with a connector portion 30 to be used as one channel. Typically, the upper electrode 3A is connected to an electric circuit via a leader line 31 with an upper electrode connection pad 32. Similarly, it is configured such that the lower electrode can be connected to an electric circuit with a lower electrode connection pad 33.

It is noted that the diaphragm 5 and the upper electrode 3 of the present embodiment are illustrated in a hexagonal shape and in the same size. However, in the present invention, such shape does not need necessarily to be a hexagonal shape, and may be another polygonal shape such as a rectangular shape, and the size does not need to be constant as well.

The substrate 1, the lower electrode 2, the diaphragm 5, the supporting wall 8, the insulator 4, and the upper electrode 3 are made of a material which can be processed with semiconductor process technology. For example, the material described in U.S. Pat. No. 6,359,367 can be used. Examples thereof include silicon, sapphire, every form of glass materials, polymers (polyimides etc.), polycrystal silicon, silicon nitride, silicon oxynitride, metal thin films (aluminum alloy, copper alloy, or tungsten, etc.), spin-on-glass (SOG), implantable doping agent or diffusion doping agent, and grown films made up of silicon oxide and silicon nitride. The interior of the cavity 7 may be vacuum or may be filled with air or any other gases. In a steady sate (non-operating state), the spacing (in the z direction) of the cavity 7 is principally maintained by the stiffnesses of the substrate 1, the diaphragm 5, the supporting wall 8, and the upper electrode 3.

Figure 3:
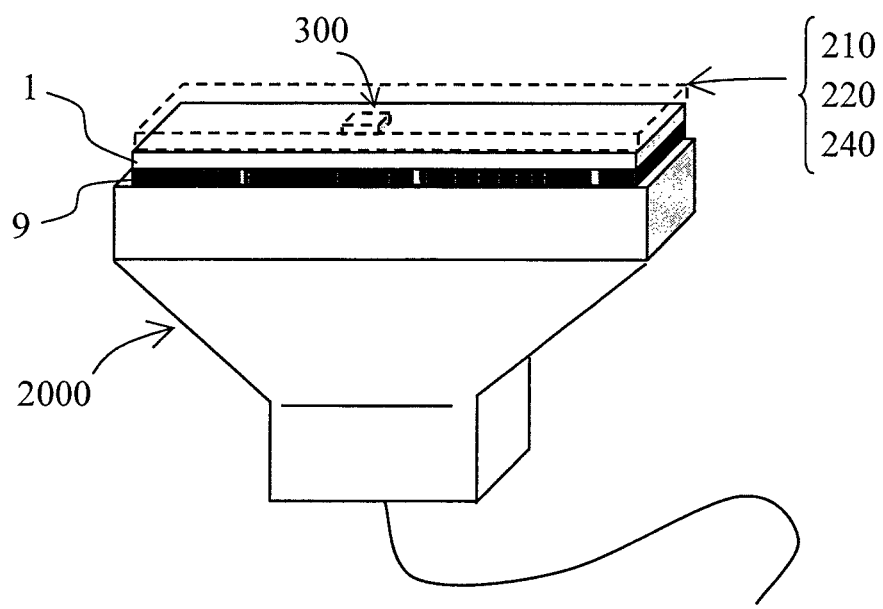
FIG. 3 is an external view of an ultrasonic probe utilizing a Capacitive Micro-machined Ultrasonic Transducer.

FIG. 3 is an exterior view when the CMUT array 300 is assembled as an ultrasonic probe 2000. The CMUT array 300 can be used with an acoustic lens 210 for causing an ultrasonic beam to converge, an acoustic matching layer 220 for matching the acoustic impedance between the CMUT and the medium (subject), and a conductive film 240 as an electrical shield layer being disposed on the medium (subject) side, and with the backing material 9 for absorbing the propagation of ultrasonic wave being provided on the back side (opposite to the medium side).

Figure 4:
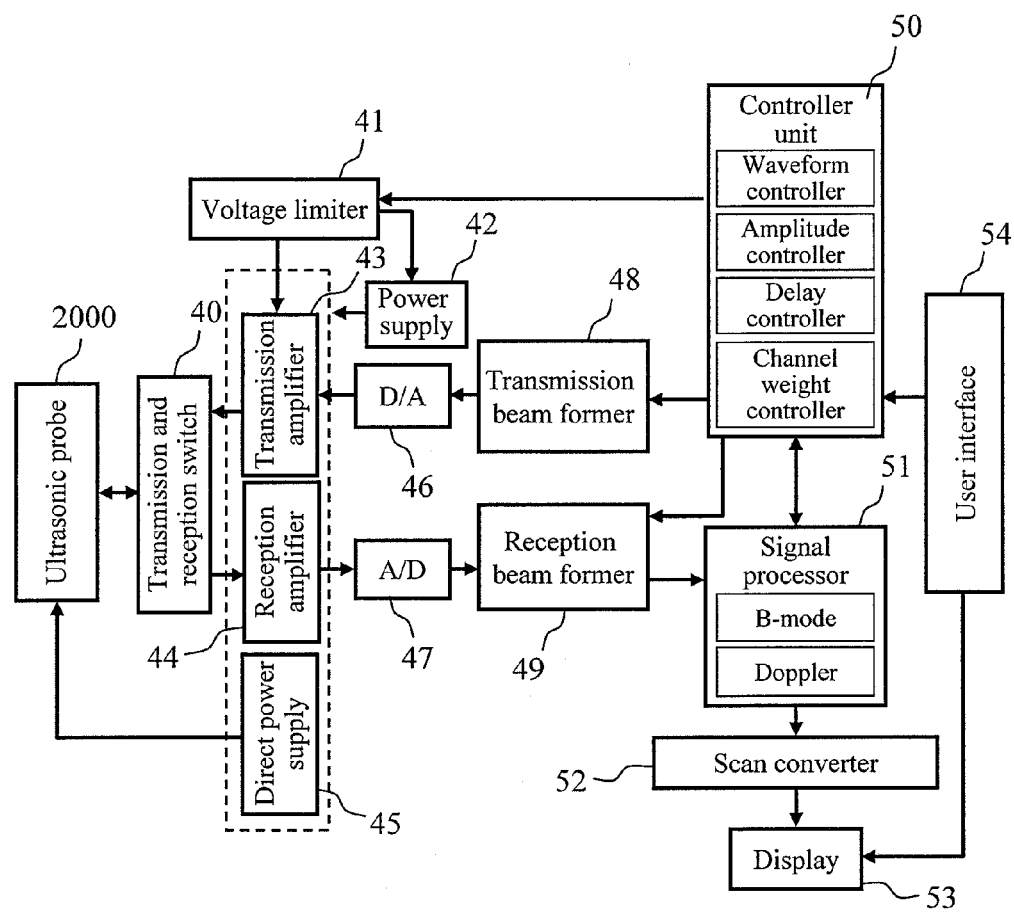
FIG. 4 is a diagram to show a system configuration example of an ultrasonic imaging device.

FIG. 4 is a diagram to show a system configuration example of an ultrasonic imaging device. As shown in FIG. 4, individual CMUT elements, or a predetermined number of grouped CMUT elements are connected to a transmission beam former 48 and a reception beam former 49 of the ultrasonic imaging device including this ultrasonic probe 2000 via a transmission and reception switch 40. The ultrasonic probe 2000 operates as an array for forming an ultrasonic beam by a direct power supply 45, a transmission amplifier 43, and a reception amplifier 44, which are driven by a power supply 42, and is utilized for the transmission/reception of ultrasonic wave. Transmitted/received signals are controlled depending on purposes by a controller unit 50. Transmitted signals are controlled by the controller unit, and a voltage is applied, in a state in which any waveform, amplitude, and delay time are set via the transmission beam former 48, a D/A converter 46, the transmission amplifier 43, to individual cells and electrodes of a channel that bundles cells. Moreover, a voltage limiter 41 is provided to prevent an excessive voltage from being applied to the probe, or for the purpose of controlling the transmission waveform. Received signals pass through the reception amplifier 44, an A/D converter 47, and the reception beam former 49, thereafter being subjected to a B-mode tomography processing or Doppler processing, and are converted into a video signal at a signal processor 51 to be displayed on a display 53 via a scan converter 52.

It is noted that the array of the CMUT array 300 shown in FIG. 2 is an example, and other array forms such as a honeycomb form, a concentric form, a grid form, and the like may be adopted. Moreover, the array plane may be planar or curvilinear, and the plane shape may be a circular shape or a polygonal shape. Alternatively, the CMUTs (10) may be arranged in a linear or curvilinear form. Moreover, part of the functions of FIG. 4 may be installed in the ultrasonic probe 2000. For example, there is no functional difference even if electric circuits such as a transmission and reception switch and a reception amplifier are incorporated in the ultrasonic probe 200.

Next, the operation principle of the CMUT will be described. The CMUT (10) functions as a variable capacitor in which a lower electrode 2 and an upper electrode 3 are disposed interposing a cavity 7 and an insulator 4 which function as a dielectric. When the upper electrode 3 is subject to a force and is displaced in the z direction, the spacing between the lower electrode 2 and the upper electrode 3 changes thereby causing the electrostatic capacity of the CMUT to change. Since the upper electrode 3 and the diaphragm 5 are joined together, the upper electrode 3 will be displaced even when a force is applied to the diaphragm 5. At this moment, when a voltage is applied between the lower electrode 2 and the upper electrode 3 and thereby an electric charge is accumulated, the temporal change of the spacing between the lower electrode 2 and the upper electrode 3 produces a temporal change of electrostatic capacity, thereby newly generating voltage between both the electrodes. In this way, when a force that causes any dynamic displacement such as ultrasonic wave; propagates to the diaphragm 5, the displacement is converted into an electrical signal (voltage or current). Moreover, a potential difference is given between the lower electrode 2 and the upper electrode 3, a charge of a different sign is accumulated on each electrode, and an attraction force is generated between the electrodes due to electrostatic force so that the upper electrode 3 is displaced toward the substrate 1. At this moment, since the upper electrode 3 and the diaphragm 5 are joined together, the diaphragm 5 is displaced at the same time. Thus, if an acoustic propagation medium such as air, water, plastic, rubber, a living body exists above (in the z direction of) the diaphragm, the displacement of the diaphragm 5 is transmitted to the medium. Temporally varying the voltage to be applied to the electrode will cause the displacement thereof to temporally vary as well, consequently resulting in sound radiation. That is, the CMUT (10) functions as an electroacoustic transducer element which can radiate an inputted electric signal to the medium adjacent to the diaphragm 5 as an ultrasonic signal, and conversely convert an ultrasonic signal from the medium into an electric signal and output the same.

Next, the mechanism through which a sound wave that propagates through the substrate is excited will be described. As described above, the CMUT (10) can perform the transmission/reception of ultrasonic wave through the vibration of the diaphragm. On one hand, the transmission and reception of ultrasonic wave is not necessarily performed only through the medium 6 which is adjacent to the diaphragm 5. For example, when a voltage is applied to the lower electrode 2 and the upper electrode 3, and the diaphragm 5 is displaced, an elastic force is generated within the diaphragm 5 as long as the diaphragm 5 is an elastic material. Since the diaphragm 5 is dynamically joined to the substrate 1 via the supporting wall 8, the force generated in the diaphragm 5 is transmitted to the substrate 1 as well. Therefore, part of the vibration energy of the diaphragm 5 propagates to the substrate 1 as well. Moreover, the electrostatic force generated between electrodes acts not only on the diaphragm 5 but also on the substrate 1 in which the lower electrode 2 is embedded. Thus, vibration propagates to the substrate 1 via electrostatic force. In this way, the CMUT has a structure in which, in principle, vibration occurs and propagates in the substrate. This vibration can propagate as various vibration modes. Examples of such modes include a longitudinal wave in which vibration propagates through repeating compression and expansion of an elastic body, a lateral wave (bending wave) in which vibration propagates through bending of the substrate, and a surface wave in which vibration occurs with a longitudinal wave and a lateral wave being combined.

Figure 5:
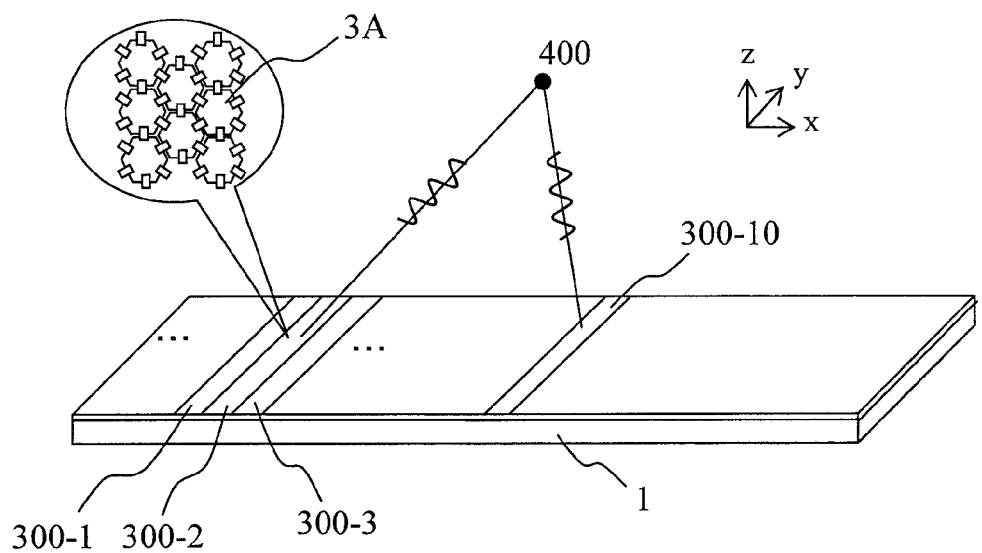
FIG. 5 is a schematic diagram of an ultrasonic transducer array and channel division.

Next, how the vibration generated in the substrate affects the reception signal of an ultrasonic probe in use will be described. First, a typical ultrasonic imaging method using the CMUT (10) will be described. FIG. 5 shows a state in which CMUTs are arrayed on a rectangular substrate 1, further a plurality of elements are formed into electrically bundled channels, and the channels are arranged in a one-dimensional strip shape. Channels 300-1, 300-2, 300-3, and 300-10 each function as the channel of a set of electroacoustic transducers. Thus, through channel division, it becomes possible to separately treat a sound wave radiated from each channel or transmission/reception electric signal. As a result, for example, in the transmission of sound wave, by adding a temporal delay to an individual voltage waveform to be applied to each channel, it is possible to match the phase of the sound wave from each channel to any point 400 on the medium which is at a different distance from each channel. That is, it becomes possible to make a focus at a certain point. Similar operation can be performed for reception signals. Performing such operation in an xz plane enables a two-dimensional imaging in the medium. It is noted that performing channel division in the y direction as well, forming a focus in the yz plane, and scanning the focus enable to perform 3-dimensional imaging.

Operating the CMUT (10) causes vibration to transmit to the substrate 1 as described above, and the vibration propagates in the substrate 1. Typically, the diaphragm 5 is a very thin film having a thickness of not more than several μm, and the substrate 1 is thicker and harder than the diaphragm.

Figure 6:
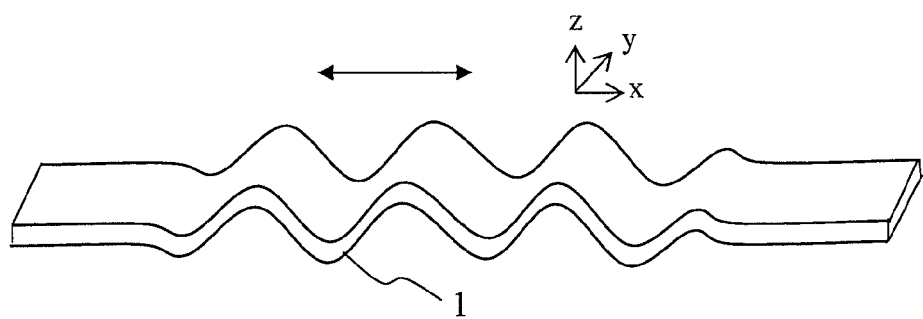
FIG. 6 is a diagram to show a state in which a lateral wave propagates.

Therefore, in considering the vibration in the substrate, it is no problem to consider a sole substrate 1 as one elastic plate neglecting the diaphragm 5. While the vibration excited in the substrate includes longitudinal waves and lateral waves, the effect of lateral waves will be considered in the present invention. FIG. 6 shows a state in which a lateral wave is traveling in a certain elastic body. As shown in FIG. 6, in a lateral wave of plate, the vibration in the vertical direction (z direction) propagates in a horizontal direction, which is the x direction (or the y direction).

Figure 7:
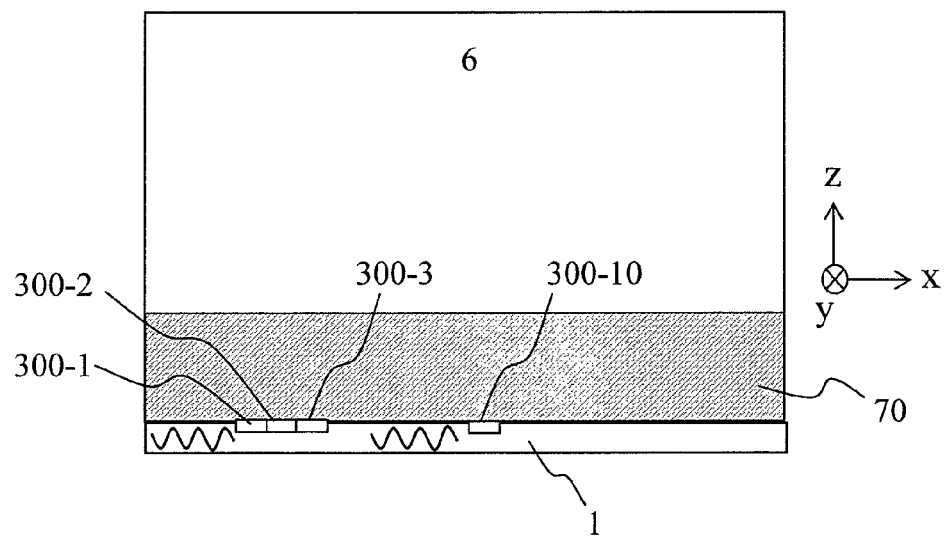
FIG. 7 is a diagram to show the effect of lateral wave on ultrasonic imaging.

Using FIG. 7, a problem when a lateral wave vibration occurs in a substrate will be shown. FIG. 7 is an x-z sectional view of the substrate seen toward the +y direction. Now suppose that a lateral wave is excited in a certain channel 300-2. The lateral wave propagates in the horizontal direction (±x directions). If the two lateral waves propagate without being attenuated, the vibration is transmitted to adjacent channels. As a result, the diaphragm in an adjacent channel vibrates as well, which is detected as a false reception signal. If a lateral wave propagates without being attenuated, it arrives at distant channels one after another and is detected as similar reception signals. When an ultrasonic transducer like a CMUT is used in channel division, since a large number of channels are caused to vibrate approximately at the same time to radiate a transmission sound wave, the above described lateral wave occurs from a plurality of channels approximately at the same time, typically causing false reception signals (artifacts) to be generated over the entire probe. However, since there is a fixed insensitive time, a so-called dead time, immediately after transmission and before the start of reception, false signals within the dead time will not become artifacts. However, if the lateral wave keeps on propagating without being attenuated even after the dead time, after transmission of an ultrasonic wave, it will become unable to distinguish that from the reflection signal from the medium 6. The time, which is required after transmission until reception of a signal, multiplied by the sound velocity of the medium of interest corresponds to a distance from the ultrasonic transducer. That is, when a false signal due to a lateral wave have continued for a fixed period of time, an artifact will be displayed in a region 70 at a certain depth from the surface of the ultrasonic transducer in a tomographic image built up of reception signals from the medium to be measured. As a result, it may become unable to evaluate the obtained results, or there is a higher risk of misevaluating the results.

Figure 8:
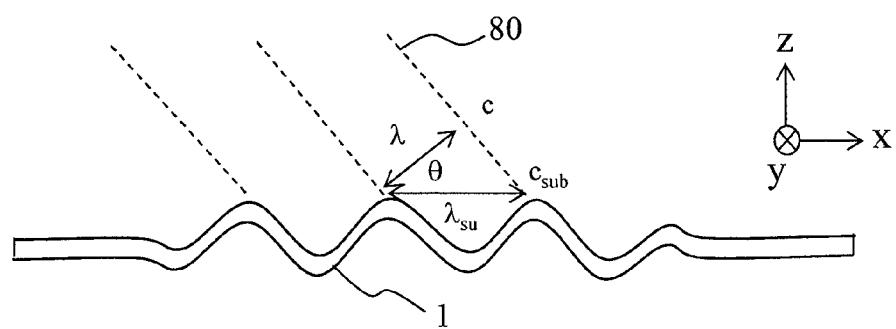
FIG. 8 is a diagram to show a state in which a lateral wave propagates in a substrate, and a state of acoustic radiation to a medium.

Next, the fundamental property and attenuation mechanism of lateral wave which causes artifacts in ultrasonic imaging will be described. FIG. 8 shows a state in which a lateral wave propagates in a substrate, and a state in which the lateral wave radiates sound to a medium adjacent to the substrate. The following relations will hold for lateral wave of an elastic plate like the substrate of CMUT:

[Expression 4]

$$c_{sub}(f) = \frac{\omega}{k_{sub}} \quad (7)$$

$$\omega = 2\pi f$$

$$k_{sub} = \frac{\sqrt{\omega}}{\alpha}$$

$$\alpha^2 = \sqrt{\frac{D}{\rho_{sub}h}} = \sqrt{\frac{Eh^2}{12\rho_{sub}(1-\nu^2)}}$$

Where, $c_{sub}$ is a lateral wave velocity [m/s] of plate, $\omega$ is an angular velocity [rad/s], f is a frequency [Hz], $k_{sub}$ is a wave number of the lateral wave of the plate, E is Young's modulus [Pa] of the plate, h is a thickness [m] of the substrate, $\rho_{sub}$ is a density [kg/m³] of the plate, and $\nu$ is Poisson's ratio of the plate. As seen from Equations (7), the sound velocity of lateral wave has a frequency dispersion relation, and the lateral-wave sound velocity $c_{sub}$ varies according to the thickness of the substrate if the material is the same.

Figure 9:
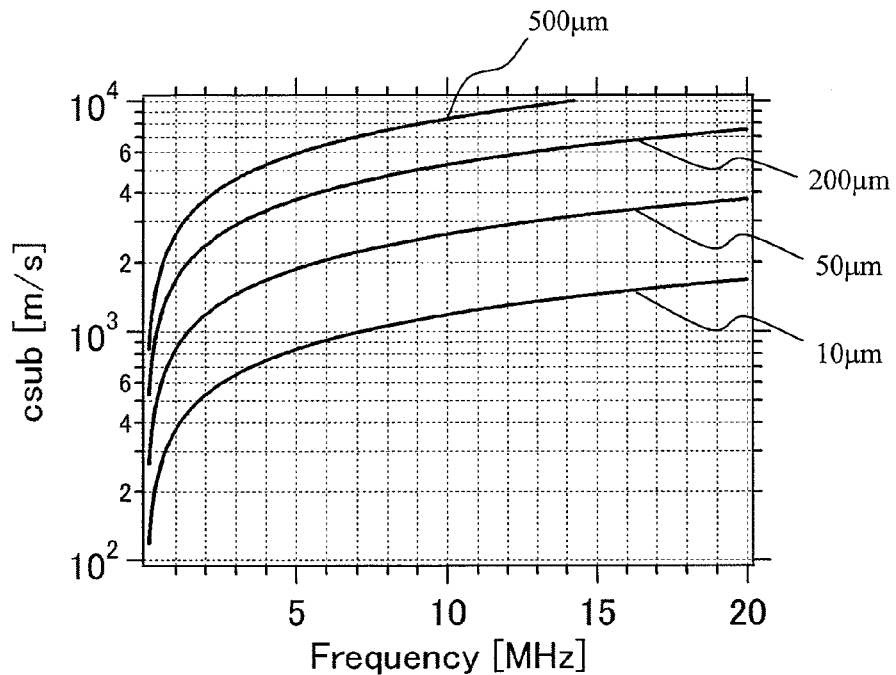
FIG. 9 is a diagram to show the frequency dependence of lateral-wave sound velocity.

FIG. 9 shows the calculation result of the lateral-wave sound velocity of silicon, which is often used as the substrate for CMUT, using the above described equations. Where, material parameters: Young's modulus E=130 [GPa], a density $\rho_{sub}$=2300 [kg/m³], and Poisson's ratio $\nu$=0.24 were used. Moreover, calculation was performed supposing that the thicknesses of the substrate were 10, 50, 200, and 500 [μm], respectively. In FIG. 9, the abscissa is frequency, and the ordinate is lateral-wave sound velocity. Paying attention to the case of a substrate thickness of 10 [μm], the higher the frequency is, the larger the lateral-wave sound velocity is, and the sound velocity sharply decreases at and less than 5 [MHz]. The curves for other substrate thicknesses show similar frequency dependence as in the case of 10 [μm]. However, as the thickness of the substrate increases, the absolute value of lateral-wave sound velocity increases.

Next, the process in which acoustic energy of the lateral wave is attenuated will be described. In general, materials such as silicon have lower energy losses within the material. For that reason, a lateral wave continues to propagate for a long period of time and its signal is detected as an artifact. If energy has not been dissipated within the substrate, there is no other way but to release it to the outside. Then, the radiation of lateral wave energy to the outside of substrate will be considered. In general, when an elastic plate such as a substrate of CMUT is in contact with a medium (any material having elasticity, such as solids, liquids, and gases) through which acoustic propagation is possible, the energy of lateral wave is radiated into an adjacent medium as acoustic energy under a certain condition. The following equations represent an acoustic radiation impedance Z(f) and a radiation angle θ(f) of a lateral wave with respect to any medium, when the substrate is in contact with the medium:

[Expression 5]

$$Z(f) = \frac{\rho c}{S} \frac{c_{sub}}{\sqrt{c_{sub}^2 - c^2}} \quad (8)$$

$$\cos\theta(f) = \frac{c}{c_{sub}}$$

Where, $c_{sub}$ and c represent the lateral-wave sound velocity of the substrate, and the longitudinal-wave sound velocity of the adjacent medium, respectively, ρ is the density of the medium, and S is the area of the substrate in contact with the medium. Moreover, the vibration that propagates into the medium herein is a longitudinal wave. That is, a lateral wave of an elastic plate is converted into a longitudinal wave and radiated into the medium. The two equations in Equation (8) are both dependent on $c_{sub}$, and since $c_{sub}$ has a frequency dependence, z and cos θ are also dependent on frequency f.

As shown in FIG. 8, the radiation angle θ(f) of longitudinal wave radiation of a lateral wave propagating in the substrate to the medium is determined from $c_{sub}$ and c, and radiation sound wave propagates forming a wavefront 80. As seen from Equation (8), when the following condition:

$$c_{sub} > c \quad (9)$$

is satisfied, the acoustic radiation impedance Z(f) of the first equation of Equation (8) becomes a real number, thus having a meaning as acoustic radiation. Thus, acoustic energy radiation to the medium can occur only when the condition of Equation (9) is satisfied. Moreover, when $$c_{sub} = c \quad (10)$$

theoretically the acoustic radiation impedance diverges to infinity. This is because the velocity of lateral wave and the sound velocity of medium becomes equal, coming into a state in which the lateral wave and the vibration of medium are always synchronized on the elastic plate surface (an in-phase state), a so-called resonance state. This frequency is referred to as a coincidence frequency $f_{co}$. Since some sort of resistance component such as friction exists in reality, there cannot exist an infinite radiation efficiency, and the radiation efficiency of lateral wave is maximized at a coincidence frequency so that a lateral wave of this frequency instantly loses energy from the substrate and is attenuated. On one hand, in the condition:

$$c_{sub} < c \quad (11)$$

Z(f) becomes an imaginary number from Equation (8), and theoretically, no acoustic energy of lateral wave will be radiated to the outside. Therefore, the lateral wave will be hardly attenuated. The radiation angle is dependent on $c_{sub}$ and c, and $c_{sub}$ will also vary depending on the frequency and physical parameters (thickness, Young's modulus, density, and Poisson's ratio) of the substrate, as well. The energy that a lateral wave of a certain frequency radiates to a medium per one cycle (one wave) is proportional to the acoustic radiation impedance Z(f) of Equation (8), the radiation energy efficiency η(f) is represented by the following equation:

[Expression 6]

$$\eta(f) = \frac{c_{sub}}{\sqrt{c_{sub}^2 - c^2}} \quad (12)$$

which is normalized by a coefficient (ρc/S) of the radiation impedance Z(f).

Figure 10:
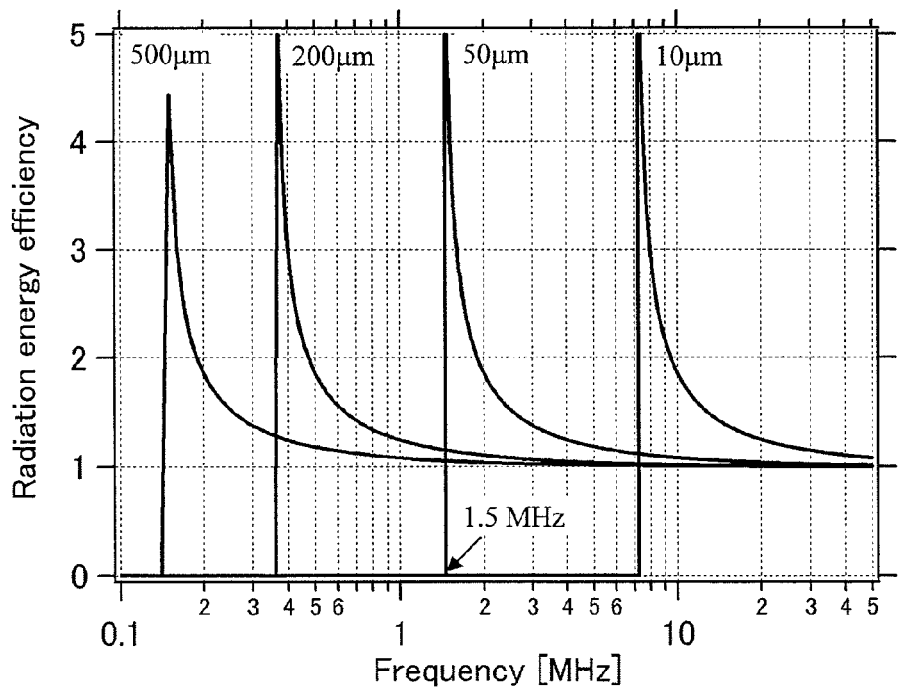
FIG. 10 is a diagram to show an acoustic radiation impedance characteristic of a substrate.

FIG. 10 shows a radiation impedance when the substrate is silicon. Here, an acoustic lens for use in an ultrasonic probe of medical diagnostic equipment is assumed as the medium. Since acoustic lenses often have a sound velocity of around 1000 [m/s], the sound velocity of the medium is supposed to be 1000 [m/s]. Moreover, as seen from FIG. 10, for example, when the substrate thickness is 50 [μm], the coincidence frequency will be around 1.5 [MHz], at which the radiation energy efficiency becomes extremely large. On the higher frequency side of the coincidence frequency, the radiation energy efficiency sharply decreases, converging to around one. On one hand, on the lower frequency side of the coincidence frequency, the radiation energy efficiency becomes zero, and the energy of lateral wave will not be radiated from the substrate. Paying attention to the dependence of the coincidence frequency on the substrate thickness, it is seen that as the substrate thickness decreases, the coincidence frequency moves to a higher frequency side.

From the above described relation between the substrate thickness and the radiation energy efficiency, the following method will be effective to reduce artifacts originated from the lateral wave. Generally, there exists a sensitive band which is effectively usable for a CMUT that is actually used. Therefore, for actual use, the attenuation efficiency of lateral wave in the sensitive band of a CMUT has a practical meaning. Accordingly, arranging that frequency band in which attenuation efficiency is high among lateral waves that have occurred overlaps the sensitive band of the CMUT transducer enables to efficiently reduce the effect of lateral wave in the band of interest.

Figure 11:
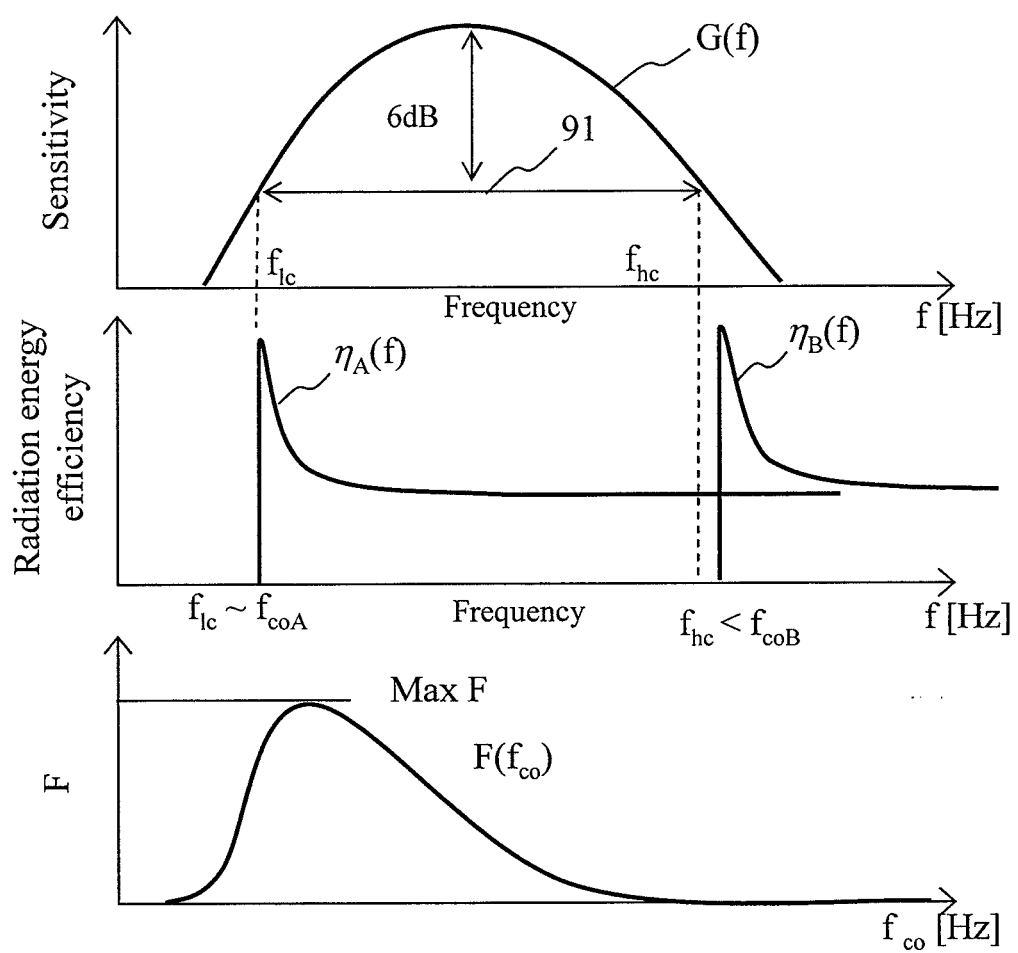
FIG. 11 is a diagram to show the relation between the frequency characteristic of sensitivity of a transducer and the lateral-wave radiation energy efficiency of the substrate, and a maximization of the lateral-wave radiation energy efficiency.

FIG. 11 shows a conceptual diagram thereof. The frequency characteristic of sensitivity of CMUT having a sensitive band 91 is represented by G(f). When letting a lower cut-off frequency of the sensitive band be $f_{lc}$, and a higher cut-off frequency be $f_{hc}$, adjusting the thickness of the substrate such that the coincidence frequency $f_{co}$ of the substrate is around $f_{lc}$ will increase the overlapping portion between the radiation energy efficiency $\eta_A(f)$ of lateral wave and the sensitive band of the transducer. The lower cut-off frequency and the higher cut-off frequency referred herein are defined such that in a transmission/reception sensitivity curve calculated from transmission/reception signals when typically an impulse-type voltage is applied to the probe, the frequencies at which a maximum value of transmission/reception sensitivity is reduced by −6 dB are determined to let the lower frequency side be the lower cut-off frequency and the higher frequency side be the higher cut-off frequency.

On one hand, as with $\eta_B(f)$ in FIG. 11, if the substrate thickness is adjusted such that the coincidence frequency is further higher than the higher cut-off frequency, since a lateral wave within the sensitive band of the CMUT radiates almost no energy to outside the substrate, a lateral wave that has once occurred will not be attenuated for a while thus producing a larger artifact. Moreover, the time for detecting the artifact will increase. Thus, to reduce artifacts caused by lateral waves and increase the practical value of CMUT, it is necessary to set appropriate substrate thickness according to the sensitive band of the CMUT.

The most effective method of practicing the present invention is the case where the substrate thickness of CMUT is adjusted such that the product between the transmission/reception sensitivity G(f) of CMUT and the lateral-wave radiation energy efficiency η(f) of the substrate becomes maximum. That is, it is equivalent to maximize the following evaluation function F:

[Expression 7]

$$F = \int \{\eta(f) \times G(f)\} df \rightarrow \max \quad (13)$$

This will allow the lateral wave component within the sensitive band to be most efficiently radiated to outside the substrate, thereby reducing the effect of artifacts.

When Equation (13) is not completely satisfied, the substrate thickness should be set at least such that the coincidence frequency $f_{co}$ of the substrate is not more than the higher cut-off frequency of the frequency characteristic of the transmission/reception sensitivity of CMUT. This will allow at least some of lateral wave energy in the sensitive band to be radiated to outside the substrate. That is, it is effective to select the substrate so as to satisfy the following equation.

$$f_{lc} \leq f_{co} \leq f_{hc} \quad (14)$$

Conversely, setting the coincidence frequency $f_{co}$ to be excessively lower than the lower cut-off frequency of the transmission/reception sensitivity of CMUT is not effective since the frequency band in which lateral waves can be radiated most efficiently and the sensitive band are not overlapped. The excessively lower frequency referred herein will be defined. Now assume that the CMUT transducer is used as a probe for medical ultrasonic diagnosis equipment. When the imaging of a living body is intended, a standard imaging region is a depth of about 10 cm from the body surface, and the lower cut-off frequency of the probe to be used is not more than about 10 MHz. The attenuation coefficient of a living body is about the same as that of water, and is 0.5 [dB/cm/MHz]. Therefore, when imaging is to be performed at 10 MHz to a depth of 10 cm, a signal transmitted from the probe undergoes an attenuation of 0.5 [dB/cm/MHz]×10 [cm]×2×10 [MHz]=100 dB in a roundtrip from a reflection point in a living body. Therefore, in such a case, the signal possessed by the probe is required to have a signal dynamic range of about 100 dB. For that reason, in medical ultrasonic diagnostic equipment, and the like, typically, a level of about 100 dB is maintained as the dynamic range of transmission/reception sensitivity. Conversely, at frequencies in the lower side, signals are at or lower than −100 dB from the transmission/reception sensitivity of the probe and are in most cases embedded in the noise level, providing no meaningful information. Therefore, a frequency in the lower frequency side at which the transmission/reception sensitivity G(f) of the probe is −100 dB from its maximum value is defined as a lower critical frequency $f_{lmin}$, and it is appropriate in the present invention to set at least such that $f_{co}$ is not less than the lower critical frequency $f_{lmin}$.

Figure 12:
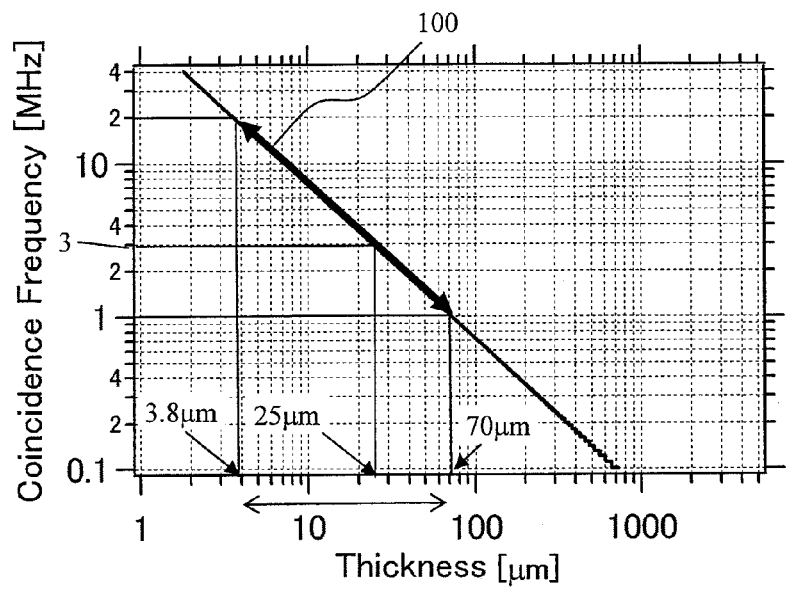
FIG. 12 is a diagram to show the relation between a substrate thickness and a coincidence frequency.

FIG. 12 shows, as an example, a relation 100 between the coincidence frequency of substrate and the substrate thickness when supposing that the substrate is silicon, and the medium in contact with the substrate is an acoustic lens (sound velocity=1000 [m/s]). As seen from FIG. 12, as the thickness of the substrate increases, the coincidence frequency decreases. In general, transducers which are generally used in medical applications often have an operation bandwidth in a range of 1 to 20 [MHz]. Supposing that an acoustic lens is used in a CMUT having a lower cut-off frequency at 3 [MHz], the substrate thickness should be set at around 25 [μm]. If it is set at not more than that, for example, 3.8 [μm], the coincidence frequency will become not less than 20 [MHz], leading to a drastic decline of the radiation efficiency of lateral wave in the sensitive band. On the contrary, since an excessively large thickness will cause the coincidence frequency to decline as seen from FIGS. 10 and 12, even though radiation occurs, the range of a highest radiation efficiency will be out of the sensitive band of CMUT. Therefore, making the substrate thickness too large will not be a good policy. In this case, when the thickness is set at 70 [μm], the coincidence frequency will become 1.0 [MHz], thus moving out of a sensitive band used in general medical applications. Therefore, in this case, the substrate thickness should be set at in a range of not less than 3.8 [μm] and not more than 70 [μm], and preferably around 25 [μm]. Although, as a matter of course, the most preferable substrate thickness will vary in accordance with the sensitive band of CMUT, it may be controlled by the optimization method of the substrate according to the method of the present invention, that is, by determining the coincidence frequency which is determined by using the abode described Equations (7) to (14), and setting the substrate thickness such that the coincidence frequency is overlapped with the sensitive band of CMUT.

It is noted that in Patent Literature 1, the substrate thickness is set at not more than 210 [μm], and the range of substrate thickness may overlap the range according to the present invention. However, the invention of Patent Literature 1 has advantages in that frequencies which are subject to the effects of multiple reflection of longitudinal wave can be moved out of the sensitive band of the probe (not less than 10 MHz), and is not intended to address lateral waves as in the present invention. Further, Patent Literature 1 gives no consideration in the energy point of view, and does not assume the attenuation of the energy of longitudinal wave. Therefore, means of the invention are different. Furthermore, although a smaller substrate thickness would be more advantageous according to Patent Literature 1, an excessively thin substrate will have no advantage according to the present invention since lateral waves are not radiated. Thus, the present invention is essentially different from Patent Literature 1 in the phenomenon, means, and effects to be addressed, and the desired form as advantages of invention.

Patent Literature 2 is intended to address lateral waves as in the present invention. However, Patent Literature 2 addresses an issue of the angle at which lateral wave is radiated from a substrate, and defines the relation between the substrate thickness d and frequency f (f×d) such that the radiation angle falls into an acceptable range of values. In this case as well, as with Patent Literature 1, it is suggested that a thinner substrate would be simply more preferable as an embodiment. In contrast to this, the present invention has focused on the point that the effects caused by lateral wave is fundamentally due to the fact that the energy of lateral wave is finite, and intends to avoid the effects of lateral wave by causing the energy of lateral wave to be actively and efficiently radiated to outside the substrate. According to the present invention, in order to cause the energy of lateral wave to be efficiently radiated to the outside, the substrate thickness should be set such that the coincidence frequency overlaps the bandwidth sensitivity of CMUT by using the above described relational Equations (7) to (14). Therefore, the substrate thickness is limited to within a specific range. Thus, the present invention is essentially different from Patent Literature 2 in the means of invention and advantages to be achieved.

Second Embodiment

Figure 13:
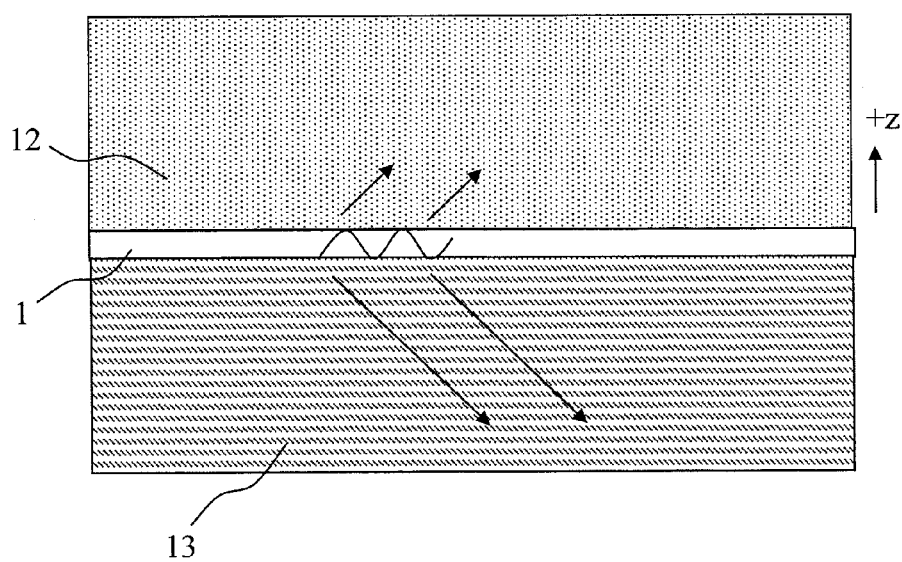
FIG. 13 is a diagram to show the state in which a medium and a backing material are in contact with the substrate.

The description of the first embodiment has supposed that the medium is an acoustic lens (sound velocity=1000 m/s). However, in actual use situations, there are cases where the CMUT is in direct contact with water and a living body 12 as shown in FIG. 13. It is noted that the structure of vibrating portion of CMUT is omitted from illustration in FIG. 13. Water and a living body have a longitudinal-wave sound velocity of about 1500 [m/s]. Since the coincidence frequency is determined from the lateral-wave sound velocity of the substrate 1 and the sound velocity of the material in contact with the substrate, an optimum substrate thickness will vary when the material in contact is changed.

Figure 14:
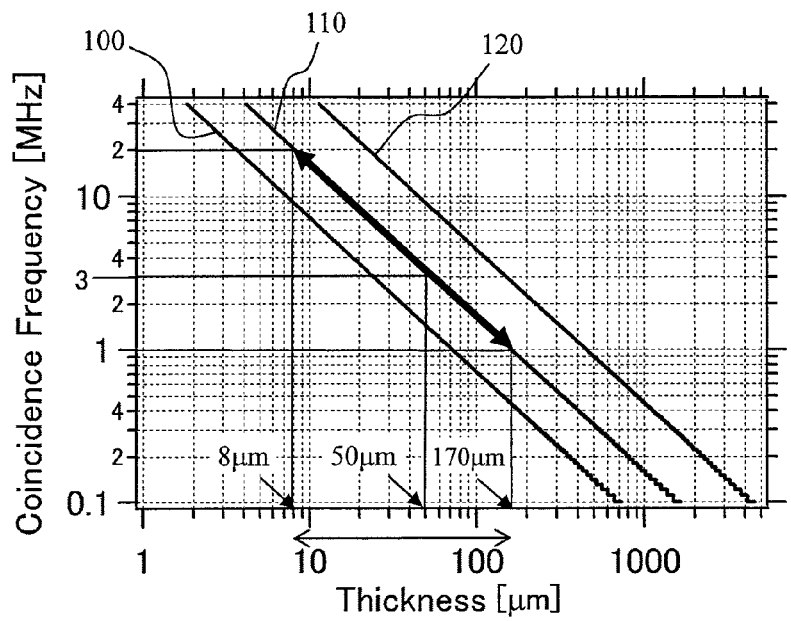
FIG. 14 is a diagram to show the relation between a substrate thickness and a coincidence frequency.

FIG. 14 shows a curve 110 of relation between the coincidence frequency and the substrate thickness when supposing that the medium in contact with the substrate is water (sound velocity is 1500 [m/s]). Supposing that a CMUT has a cut-off frequency at 3 [MHz] and the medium is water, when the substrate thickness is about 50 [μm], the coincidence frequency will become 3 [MHz], thereby satisfying the condition of the present invention. Although an optimum coincidence frequency cannot be uniquely determined since it varies depending on the sensitive band of CMUT, supposing that the most frequently used band of the transducer is approximately 1 to 20 [MHz], it is seen that according to the present invention, the substrate thickness falls into a range of 8 [μm] to 170 [μm] as seen in FIG. 14. An optimum value in the sensitive band of individual CMUT may be set such that the coincidence frequency overlaps the sensitive band of the CMUT according to the procedure of the determination of substrate thickness of the present invention. It is noted that FIG. 14 also shows at the same time the relation 100 between the coincidence frequency and the substrate thickness when the medium in contact with the substrate is an acoustic lens (sound velocity=1000 [m/s]) which is shown in FIG. 12.

Third Embodiment

In the above described two embodiments, it is supposed that in the medium, the energy of lateral wave is radiated toward the upper side (+z side) of CMUT. The use method of ultrasonic probe includes a case in which a backing material 13 is bonded to the underside (−z side) as shown in FIG. 13. It is often the case that a resin or metal having a sound velocity of 2000 to 3000 [m/s] is used as the backing material. As in the second embodiment, since the coincidence frequency is determined from the lateral-wave sound velocity of the substrate 1 and the sound velocity of the material in contact, an optimum substrate thickness will vary when the material in contact is changed.

Figure 15:
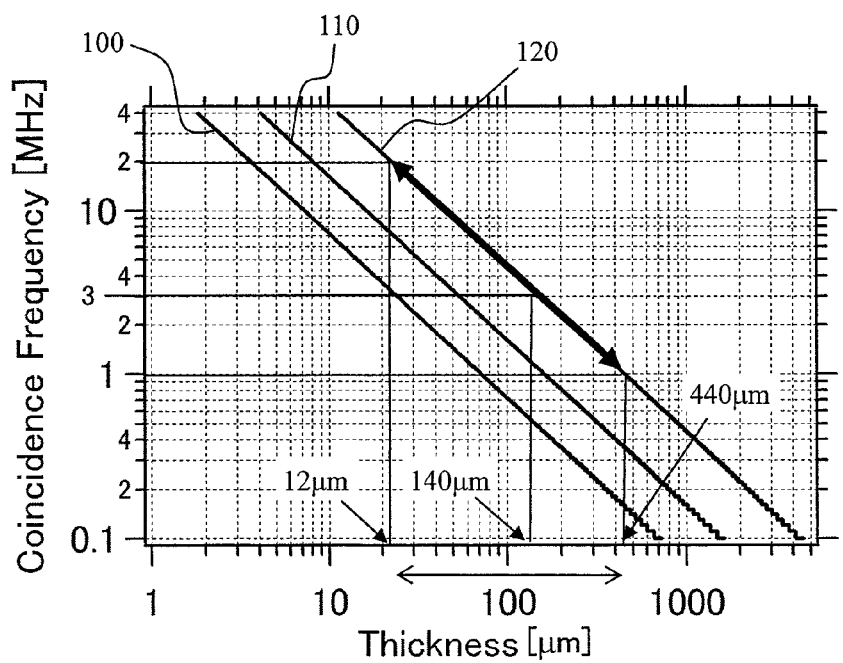
FIG. 15 is a diagram to show the relation between a substrate thickness and a coincidence frequency.

FIG. 15 shows a curve 120 of relation between the coincidence frequency and the substrate thickness when supposing that the medium into which acoustic energy is radiated is a backing material (sound velocity=2500 [m/s]). The substrate thickness when the coincidence frequency is set at 3 [MHz] will be about 150 [μm] when the medium is the backing material. Supposing that the most frequently used band of the transducer is approximately 1 to 20 [MHz], it is seen that according to the present invention, the substrate thickness falls into a range of 12 [μm] to 440 [μm] as seen in FIG. 15. An optimum value in the transmission/reception sensitive band of individual CMUT may be set such that the coincidence frequency overlaps the sensitive band of the CMUT according to the procedure of the determination of substrate thickness of the present invention.

Fourth Embodiment

Figure 16:
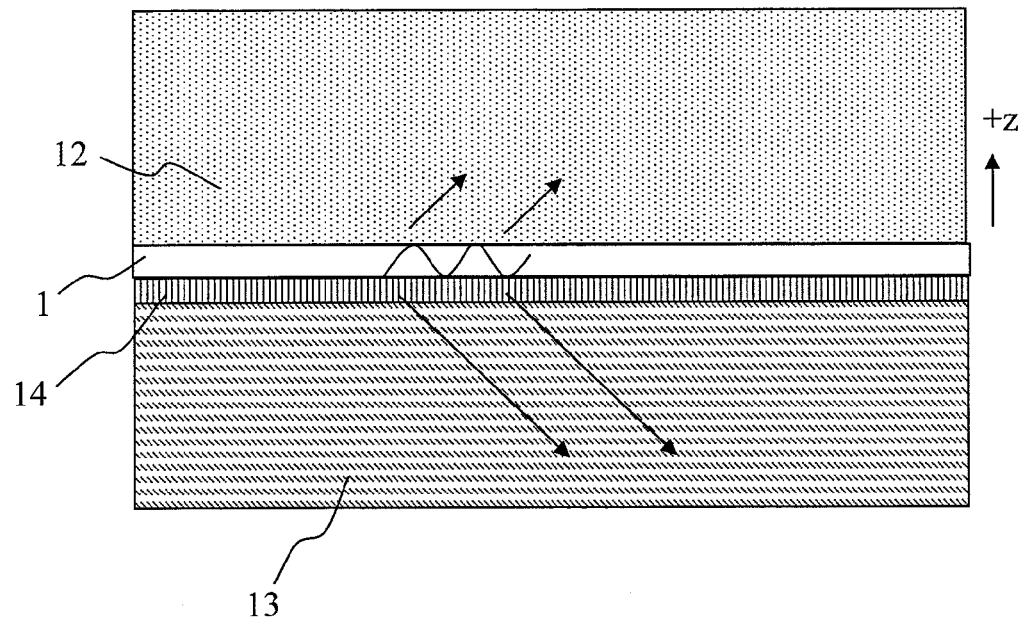
FIG. 16 is a diagram to show the state in which a medium is in contact with the substrate and a backing material is mounted via an adhesive.

In the third embodiment, it is supposed that the backing material is directly in close contact with the substrate. However, as shown in FIG. 16, in reality, the substrate and the backing material are often bonded together with some sort of adhesive 14. At this moment, since the energy radiation of lateral wave into the baking material takes place via the adhesive material, a substrate thickness slightly different from that of the third embodiment will become an optimum value. The thickness of adhesive layer is typically several μm to several tens and its sound velocity is mostly around 1000 to 2000 [m/s]. At this time, the wavelength of 10 [MHz] will be 100 to 200 [μm]. Therefore, it cannot be said that the thickness of adhesive layer is sufficiently small with respect to the wavelength of longitudinal wave within the adhesive material. When the thickness is not sufficiently small with respect to the wavelength, it cannot be neglected in an acoustic sense and the adhesive layer functions as a medium. For this reason, when a baking material is bonded to the substrate via an adhesive, the sound velocity of the adhesive material becomes important. As described in the second and third embodiments, since the sound velocity of water is about 1500 [m/s] and that of the backing material is about 2000 to 3000 [m/s], the sound velocity of the adhesive material would be an intermediate value thereof. Therefore, an optimal substrate thickness is included between the case of water and the case of the backing material. Performing the calculation as in the above described first to third embodiments according to the procedure of the present invention will result in that approximately 15 to 300 [μm] will be a preferable substrate thickness for the radiation of lateral wave energy.

Fifth Embodiment

Figure 17:
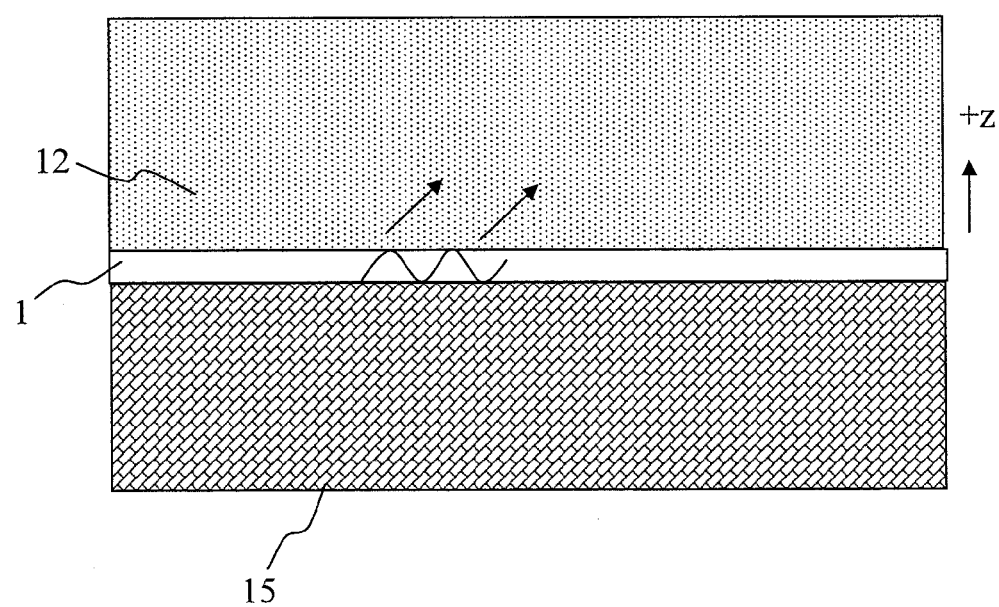
FIG. 17 is a diagram to show the state in which an electronic circuit is in contact immediately beneath the substrate.

In the present invention, an electronic circuit 15 can be mounted onto the underside of CMUT as shown in FIG. 17. When the material of the electronic circuit of the portion in contact with the CMUT is a typical plastic substrate, the sound velocity thereof will be comparable to those of the adhesive and the backing material as described in the third and fourth embodiments, the optimal substrate thickness will be around those of the third and fourth embodiments. On one hand, when an electronic circuit is constructed directly beneath the substrate by a semiconductor process, the sound velocity of the electronic circuit will become close to that of the silicon substrate, being a significantly high value (for example, 8000 [m/s]). In this case, since the coincidence frequency will not be fit into a normal transmission/reception sensitive band of CMUT, there is no way but to radiate much of lateral wave energy from the front side. In this case, an optimum substrate thickness will be those according to the first or second embodiment.

Figure 18:
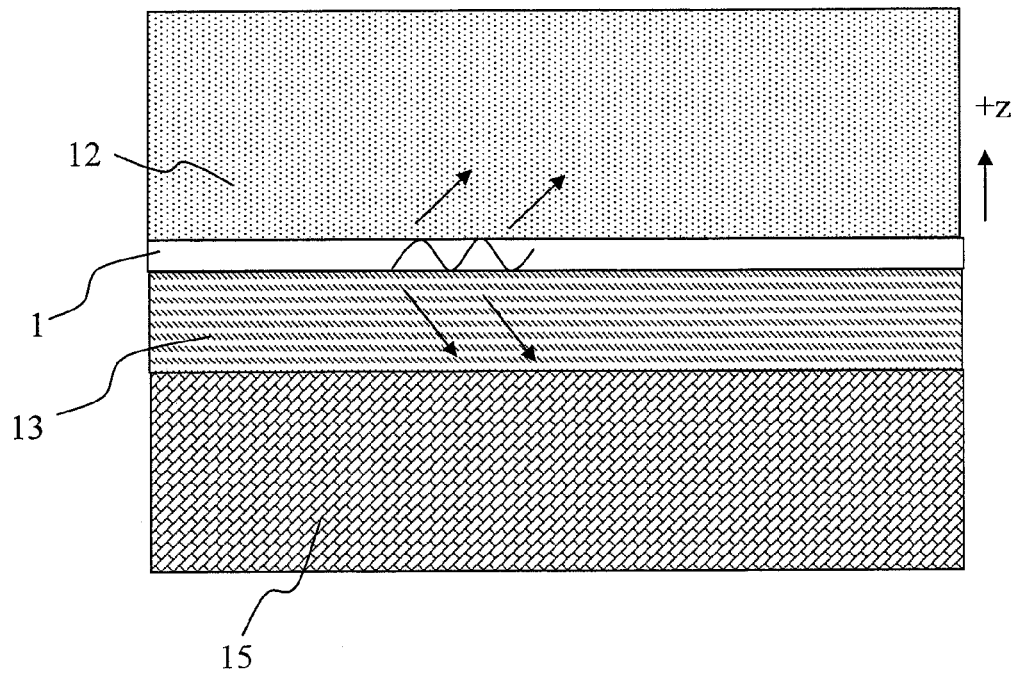
FIG. 18 is a diagram to show the state in which an electronic circuit is mounted in contact immediately beneath the substrate via the backing material.

Moreover, the electronic circuit 15 may be disposed via a backing material 13 without being in direct contact with the substrate, as shown in FIG. 18. In this case, it is a matter of course that an optimum substrate thickness for attenuating lateral waves will be about the same as those of the third or fourth embodiments.

Sixth Embodiment

Figure 19:
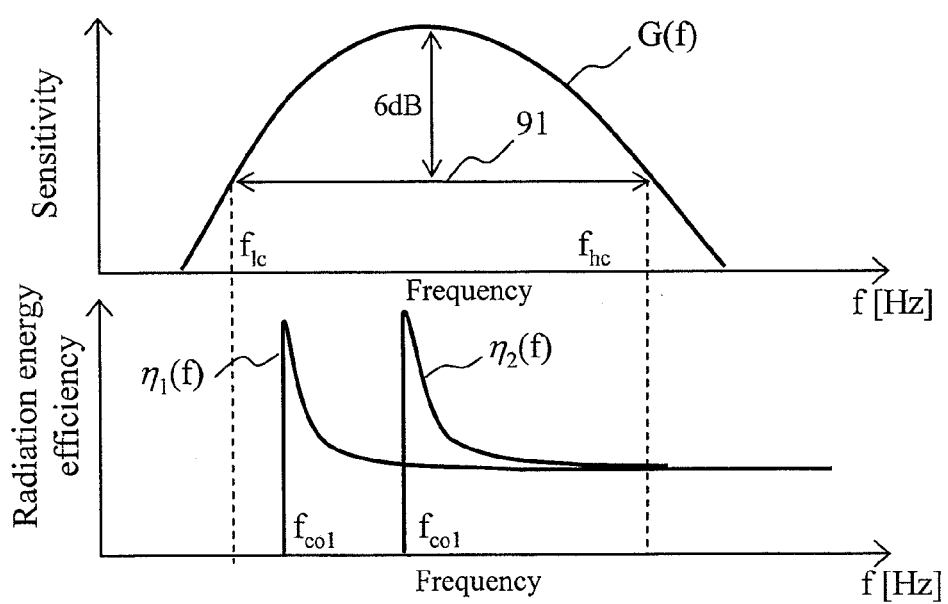
FIG. 19 is diagram to show the relation between the frequency characteristic of sensitivity of a transducer and the lateral-wave radiation energy efficiency of the substrate when a plurality of acoustic media are in contact with the transducer.

In the above described first to fifth embodiments, only the relation between a single acoustic medium and a substrate has been described. However, it is often the case that a CMUT that is actually used as a probe is in contact with an acoustic medium on both the front and back sides. In this case, the energy of lateral wave will be radiated to both the front and back sides. When the acoustic media of the front and back sides are different, especially when sound velocities thereof are different, the optimum substrate thicknesses for the front and back sides will be of course different from each other. The method for setting a substrate thickness when the CMUT is in contact with such a plurality of acoustic media will be presented below. FIG. 19 shows a conceptual diagram of the present embodiment. When two different acoustic media are in contact with the front and back sides of CMUT, the radiation energy efficiencies of lateral wave with respect to respective acoustic media are represented as $\eta_1(f)$ and $\eta_2(f)$. When sound velocities of respective acoustic media are different from each other, the respective coincidence frequencies $f_{co1}$ and $f_{co2}$ are also different, and consequently the ranges overlapping the transmission/reception sensitivity $G(f)$ will be different. In such a case, in the viewpoint of maximizing the radiation energy efficiency of lateral wave, it is preferable that the following condition is satisfied:

[Expression 8]

$$F = \sum_N \int \{\eta_N(f) \times G(f)\} df \to \max \tag{15}$$

Where, N is the number (N=1, 2, ...) of the acoustic medium in contact with the substrate, $\eta_N(f)$ is the lateral-wave radiation energy efficiency with respect to individual acoustic medium, and G(f) is the transmission/reception sensitivity of the CMUT probe. When satisfying Equation (15), the lateral wave energy that affects imaging is most efficiently radiated from the substrate.

Seventh Embodiment

In the sixth embodiment, all of the plurality of coincidence frequencies are not necessarily fit into the transmission/reception sensitive band of CMUT at the same time. In such a case, the coincidence frequency of backside material side should be preferentially fit into the sensitive band. Because the energy of lateral wave radiated to the front side may be reflected back as a sound from any reflection source in an object to be imaged, thus producing undesired signal components. Therefore, when the coincidence frequency is significantly different between the front and back sides, and both cannot be fit into the transmission/reception sensitive band of CMUT at the same time, the substrate thickness should be set such that the coincidence frequency corresponding to the medium in contact with the back side of substrate, which is opposite to the object to be imaged, is optimized according to Equation (13).

REFERENCE SIGNS LIST

1: Substrate
2: Lower electrode
3A: Upper electrode
3B: Upper electrode
3C: Upper electrode
4: Insulator
5: Diaphragm
6: Medium
7: Cavity
8: Supporting wall
9: Backing material
10: Capacitive Micro-machined Ultrasonic Transducer
12: Front side medium
13: Backside material (backing material)
14: Adhesive
15: Electronic circuit
30: Connector portion
31: Leader line
32: Upper electrode connection pad
33: Lower electrode connection pad
40: Transmission and reception switch
41: Voltage limiter
42: Power supply
43: Transmission amplifier
44: Reception amplifier
45: Direct power supply
46: D/A CONVERTER
47: A/D CONVERTER
48: Transmission beam former
49: Reception beam former
50: Controller unit
51: Signal processor
52: Scan converter
53: Display
54: User interface
70: Artifact region
80: Wavefront of sound wave formed by acoustic radiation to medium by lateral wave
91: Sensitive band
100: Relation between coincidence frequency and substrate thickness (medium is acoustic lens)
110: Relation between coincidence frequency and substrate thickness (medium is water)
120: Relation between coincidence frequency and substrate thickness (medium is backing material)
210: Acoustic lens
220: Acoustic matching layer
240: Conductive film
300: Ultrasonic transducer array
400: Focus
2000: Ultrasonic probe
G(f): Frequency characteristic of sensitivity
$\eta_A(f)$: Characteristic of radiation energy efficiency of lateral wave when coincidence frequency is near lower cut-off of sensitive band
$\eta_B(f)$: Characteristic of radiation energy efficiency of lateral wave when coincidence frequency is near higher cut-off of sensitive band
F(f): Evaluation function of lateral wave energy radiation
$\eta_1(f)$: Coincidence frequency for medium 1
$\eta_2(f)$: Coincidence frequency for medium 2

The invention claimed is:

1. An ultrasonic probe, comprising:
a Capacitive Micro-Machined Ultrasonic Transducer, wherein the Capacitive Micro-Machined Ultrasonic Transducer comprises:
a substrate comprising a first electrode and a lateral-wave sound velocity; and
a diaphragm having a second electrode,
wherein the diaphragm is connected at its peripheral edge to the substrate via a supporting wall which rises from the substrate, and a cavity is formed between the substrate and the diaphragm,
wherein the lateral-wave sound velocity, at least in a fractional frequency band within a sensitive band of the ultrasonic probe, is not less than a longitudinal-wave sound velocity of a medium in contact with the substrate or the diaphragm, and
wherein a coincidence frequency of the substrate with a medium in contact with the substrate or the diaphragm is present in the sensitive band.

2. The ultrasonic probe according to claim 1, wherein the coincidence frequency of the substrate for a medium in contact with the substrate or the diaphragm is not higher than a higher cut-off frequency of the sensitive band.

3. The ultrasonic probe according to claim 1, wherein the coincidence frequency of the substrate for a medium in contact with the substrate or the diaphragm is not lower than 1/10 of a lower cut-off frequency of the sensitive band.

4. The ultrasonic probe according to claim 1, wherein an acoustic lens is provided on an acoustic radiation surface of the ultrasonic transducer.

5. The ultrasonic probe according to claim 4, wherein the substrate has a thickness of not less than 3.8 µm and not more than 70 µm.

6. The ultrasonic probe according to claim 1, wherein water or a living body is brought into contact with an acoustic radiation surface of the ultrasonic transducer when in use.

7. The ultrasonic probe according to claim 6, wherein the substrate has a thickness of not less than 12 µm and not more than 170 µm.

8. The ultrasonic probe according to claim 1, wherein a backing material is provided on a substrate side of the ultrasonic transducer.

9. The ultrasonic probe according to claim 1, wherein an acoustic lens, or water or a living body is brought into contact with an acoustic radiation surface of the ultrasonic transducer, and a backing material is provided on a substrate side thereof.

10. The ultrasonic probe according to claim 8 or 9, wherein the substrate has a thickness of not less than 12 μm and not more than 440 μm.

11. The ultrasonic probe according to claim 1, wherein a backing material is bonded to a substrate side of the ultrasonic transducer with an adhesive.

12. The ultrasonic probe according to claim 11, wherein the substrate has a thickness of not less than 15 μm and not more than 300 μm.

13. The ultrasonic probe according to claim 1, wherein an electronic circuit is provided on a substrate side of the ultrasonic transducer.

14. The ultrasonic probe according to claim 13, wherein the substrate has a thickness of not less than 15 μm and not more than 300 μm.

15. The ultrasonic probe according to claim 1, wherein a thickness h of the substrate is set such that the coincidence frequency satisfies the following conditions:

$$c_{sub} = \frac{\omega}{k_{sub}}$$

$$\omega = 2\pi f$$

$$k_{sub} = \frac{\sqrt{\omega}}{\alpha}$$

$$\alpha^2 = \sqrt{\frac{Eh^2}{12\rho_{sub}(1-v^2)}}$$

wherein $c_{sub}$ is a lateral wave velocity of plate,
wherein $\omega$ is an angular velocity,
wherein f is a frequency,
wherein $k_{sub}$ is a wave number of the lateral wave of the substrate,
wherein E is a Young's modulus of the substrate,
wherein h is the thickness of the substrate,
wherein $\rho_{sub}$ is a density of the substrate, and
wherein v is a Poisson's ratio of the substrate.

* * * * *